United States Patent [19]

Hampton

[11] 4,360,931
[45] Nov. 30, 1982

[54] PROSTHETIC ANKLE

[76] Inventor: Ralph C. Hampton, 18881 Gentian Ave., Riverside, Calif. 32504

[21] Appl. No.: 254,306

[22] Filed: Apr. 15, 1981

Related U.S. Application Data

[63] Continuation-in-part of Ser. No. 47,866, Jun. 12, 1979, abandoned.

[51] Int. Cl.³ .............................. A61F 1/04; A61F 1/08
[52] U.S. Cl. ................................................. 3/32; 3/7
[58] Field of Search ....................................... 3/30–35, 3/7, 2

[56] References Cited

U.S. PATENT DOCUMENTS

| | | | |
|---|---|---|---|
| 25,238 | 8/1859 | Bly | 3/32 |
| 608,812 | 8/1898 | Weller | 3/32 |
| 817,340 | 4/1906 | Rosenkranz | 3/32 |
| 1,001,641 | 8/1911 | Harrison | 3/32 |
| 1,285,871 | 11/1918 | Winn | 3/32 |
| 2,439,195 | 4/1948 | Witmyer et al. | 3/32 |
| 2,594,945 | 4/1952 | Lucas et al. | 3/32 |
| 3,481,332 | 12/1969 | Arnold | 3/2 X |
| 3,940,804 | 3/1976 | Benton et al. | 3/33 X |
| 3,956,775 | 5/1976 | Moore | 3/33 |
| 3,982,280 | 9/1976 | Asbelle et al. | 3/32 |

FOREIGN PATENT DOCUMENTS 1371996 10/1974 United Kingdom ...................... 3/7

Primary Examiner—Ronald L. Frinks
Attorney, Agent, or Firm—Herbert E. Kidder; John H. Crowe

[57] ABSTRACT

A prosthetic ankle for use between the ankle block forming the bottom end of a prosthetic lower leg, and a prosthetic foot, comprising a securing bolt extending upwardly through a hole in the foot and screwed into a nut in the ankle block. Under the head of the bolt are two cupped washers that provide a ball-and-socket connection which allows angular movement of the ankle block in all directions with respect to the foot, as well as rotational movement. A pad of elastomeric material is interposed between the top surface of the foot and the bottom surface of the ankle block, and is cemented to the top surface of the foot. The pad is of a thickness and hardness such that when the ankle block is leaned in any direction, the elastomeric material on the inside of the lean is compressed. Pins project downwardly from the bottom surface of the ankle block and are received in cavities in the elastomer. When a torsional stress is exerted on the ankle block, the pins exert a torsional in the elastomer. When the torsional stress is released, the elasticity of the elastomer causes the foot to be returned to the straight-ahead position.

3 Claims, 8 Drawing Figures

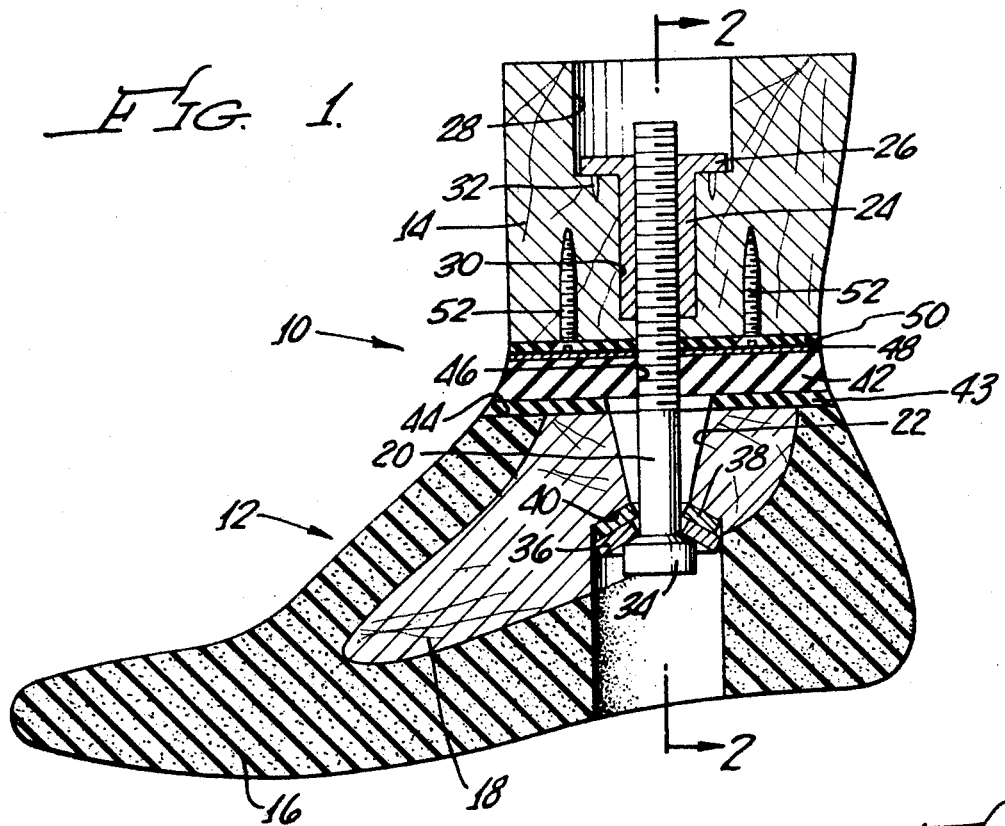
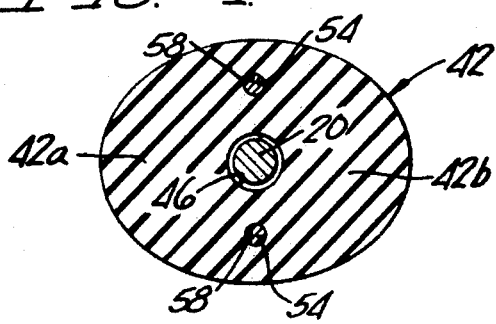
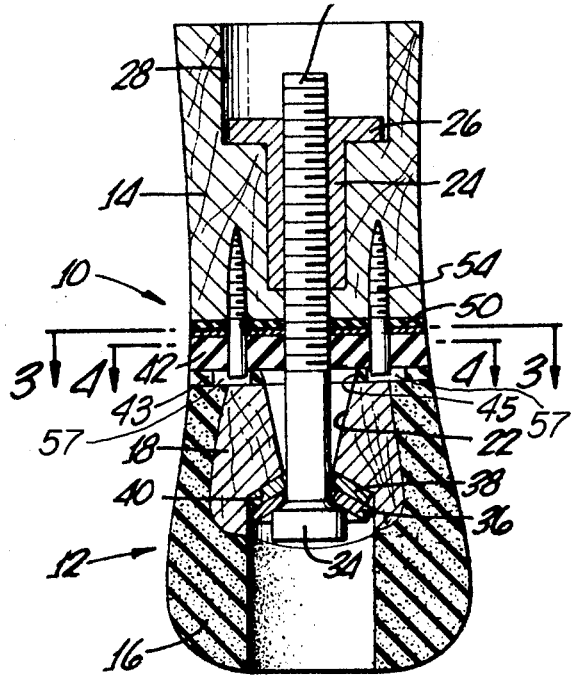

PROSTHETIC ANKLE

BACKGROUND OF THE INVENTION

The present invention pertains to prosthetic devices, and is a continuation-in-part of my pending application Ser. No. 47,866, filed June 12, 1979, now abandoned. More particularly, the invention pertains to an ankle prosthesis having certain capabilities that have heretofore not been available.

There are only a few prosthetic ankles on the market that provide any relative movement between the lower leg and the foot, and all of these have serious drawbacks that make them unattractive to most amputees. For example, one device, known as a "rotator" provides a limited amount of rotation, which enables the wearer to twist the lower leg relative to the foot. However, this rotator provides no angular movement between the lower leg and foot, and angular movement is the most important function of the natural ankle in walking. In addition to being quite expensive, the rotator has another serious disadvantage, in that it is relatively heavy, and the wearer is constantly aware that he is carrying the weight of the device at the bottom end of his leg.

Another prosthetic ankle that is available on the market provides for angular movement of the lower leg in two planes of rotation, but since the natural ankle has the capability of angular movement in all directions, this device leaves much to be desired. This device is also quite expensive, and its weight is so objectionable that few amputees can put up with it. As a result, the device is little used.

In the great majority of cases, the prosthetic foot is solidly and rigidly attached to the lower leg so that there is no relative movement between them, and the wearer relies on the limited flexibility of the foot to enable him to walk in a stiff-legged manner.

SUMMARY OF THE INVENTION

The primary object of the present invention is to provide a new and improved prosthetic ankle that more closely simulates the movements of a natural ankle than any other prosthetic ankle that has been placed on the market.

More specifically, it is the object of the invention to provide a prosthetic ankle capable of passive angular movement in all directions as the wearer puts his weight first on the heel and then on the ball of the foot in walking, or as he leans the lower leg in any direction while carrying his weight on the foot.

Another important object of the invention is to provide a prosthetic ankle having the capability of rotation in either direction to a degree approximating the rotation of the natural ankle. A highly desirable feature of the invention is that the foot is returned to its normal, straight-ahead position when the angular or rotational stress is removed.

A further object of the invention is to provide a prosthetic ankle that is extremely light in weight and, in fact, adds only a few ounces to the weight of the foot without the ankle.

Other objects are to provide a prosthetic ankle that is capable of being used with most existing prosthetic feet; and that is totally silent in operation; simple and inexpensive to manufacture; and rugged in construction, with virtually nothing to wear or get out of order.

The foregoing objects are achieved by providing a connector to join the foot to the lower leg, which allows angular movement between them in all directions, as well as rotational movement, together with a pad of elastomeric material between the foot and the lower leg which is compressible under angular movement, and which is torsionally stretched in shear to allow for rotational movement. The pad of elastomeric material is placed between opposed surfaces on the foot and lower leg, and is cemented or otherwise secured to one of the surfaces, while the other surface is freely rotatable relative to the elastomeric pad, but is yieldingly constrained against rotational movement by pins, or other projections, that extend from the other surface into cavities in the elastomeric pad. Thus when the said other surface is twisted relative to the one surface about a horizontal axis, the pins or projections are caused to twist the elastomer. The elastomer, being elastic, yields under the torsional stress, allowing the lower leg to twist relative to the foot through an angular distance of some 15 or 20 degrees to either side of straight ahead.

These and other objects and advantages of the invention will become apparent to those skilled in the art from the following detailed description of the presently preferred embodiment of the invention, together with the drawings.

BRIEF DESCRIPTION OF THE DRAWINGS

FIG. 1 is a vertical section through a portion of the lower leg and foot prosthesis, which are joined together by the prosthetic ankle of the invention;

FIG. 2 is a transverse section through the same, taken at 2—2 in FIG. 1;

FIG. 3 is a horizontal section taken at 3—3 in FIG. 2;

FIG. 4 is another horizontal section taken at 4—4 in FIG. 1;

DESCRIPTION OF THE PREFERRED EMBODIMENT

Figure 5:
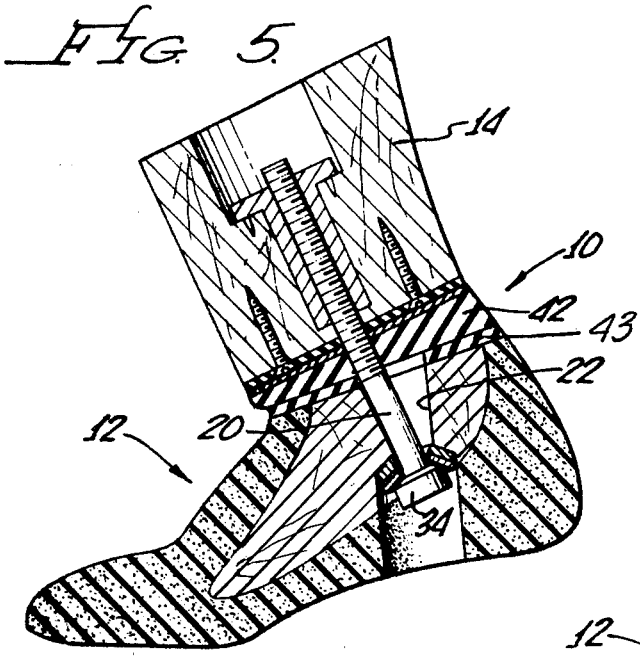
FIGS. 5 and 6 are views similar to FIG. 1, showing the fore-and-aft angular movement of the lower leg with respect to the foot.

In the drawings, the ankle of the present invention is designated in its entirety by the reference numeral 10, and connects foot 12 to ankle block 14 of wood, which is mounted at the bottom end of the prosthetic lower leg. The prosthetic lower leg, itself, is usually made of fiberglass-reinforced plastic molded to approximate the configuration of the missing natural leg, and the ankle-block 14 is either molded into the prosthetic leg, or otherwise attached thereto.

The foot 12 is a widely used, conventional prosthetic foot, consisting of a firm grade of foam elastomer 16 molded over a wood keel 18. The foot 14 is secured to the ankle block 14 by means of a long bolt 20 which extends upwardly through a conically enlarged, bell-shaped aperture 22 in the keel 18 and is screwed into an elongated, internally threaded nut 24 having a radial flange 26 at its upper end that is seated on the shoulder formed at the junction of an enlarged bore 28 with a reduced-diameter bore 30, through which the nut 24 extends. The flange 26 has downwardly projecting barbs 32 on its underside that penetrate into the wood of the ankle block to prevent the nut 24 from turning.

Seated under the head 34 of the bolt is a spherically or conically cupped washer 36, which bears against a similarly spherically or conically cupped, larger washer 38, that is seated against an annular shoulder 40 formed at the bottom end of aperture 22. Bolt head 34 has the usual hexagonal socket formed in its bottom, to receive an Allen wrench. When bolt 20 is drawn up snugly to the position shown in FIGS. 1 and 2, washers 36 and 38 function in the manner of a ball and socket, allowing the lower leg (as represented by the ankle block 14) to swing in all directions. At the same time, the bolt 20 and washer 36 are free to turn in rotation about the washer 38. The bell-shaped aperture 22 allows the bolt 20 to lean in all directions, as best shown in FIGS. 5–8. In all cases, it will be noted that the sides of the conically enlarged, bell-shaped aperture 22 are cut back far enough so that the bolt 20 does not contact the aperture sides when the lower leg is leaned to the maximum extent in any direction.

Interposed between the ankle block 14 and foot 12 is a pade of elastomer, the presently preferred material being polyurethane. The pad 42 may typically be about ½ inch thick, although this dimension is not critical and might be considerably greater, or slightly smaller. The pad is cemented to a flat plate 43 of nylon, or other low-friction plastic material, which is cemented, in turn, to the top surface 44 of the foot. Plate 43 forms a flat, hard surface that covers the top surface of the keel 18 and its foam covering 16, and provides a hard, flat base for the pad 42. The plate 43 thus protects the pad 42 from indentation by the sharp edges of the keel 18 at the points where the keel ends and the soft foam 16 begins. Plate 43 is preferably about ⅛ inch in thickness, and has a central hole 45 of the same size and shape as the opening at the to end of aperture 22. The outer edges of the pad 42 are faired into the outer surfaces of the foot 12, and a hole 46 is provided in the center of the pad to allow the bolt 20 to pass through and thus turn freely therein.

Cemented to the top surface of the pad 42 is a sheet 48 of Teflon or other slippery material, which bears against a thin plate 50 of Kydex, another slippery plastic material. Plate 50 is secured by screws 52 to the bottom surface of the ankle block 14. Plate 50 thus turns freely and with very little friction on Teflon sheet 48, while pad 42 is fixedly cemented to foot 12, and does not turn with respect thereto.

As shown in FIG. 2, there are two pins 54 with wood-screw threads, that are screwed into the bottom end of ankle block 14 on opposite sides of the bolt 20. Pins 54 project downwardly through holes in plate 50 and arcuate slots 56 in Teflon sheet 48, and pass through snug-fitting openings 58 (see FIG. 4) in pad 42. The bottom ends of the pins 54 project below the bottom surface of the pad 42, and are received within arcuate slots 57 (see FIG. 2) in plate 43, which are similar to slots 56 but somewhat wider than the latter so as to accommodate lateral movement of the pins 54 when the leg is tilted to one side or the other.

When the wearer places a torsional stress on the ankle block 14, the plate 50 turns on the Teflon sheet 48, and pins 54 twist the elastomeric pad 42 in shear. The rotational movement of the pins 54 is accommodated by the slots 56 and 57. When the torsional stress is removed, the elasticity of the pad 42 causes the pins 54 to be turned back to their original position.

Figure 6:
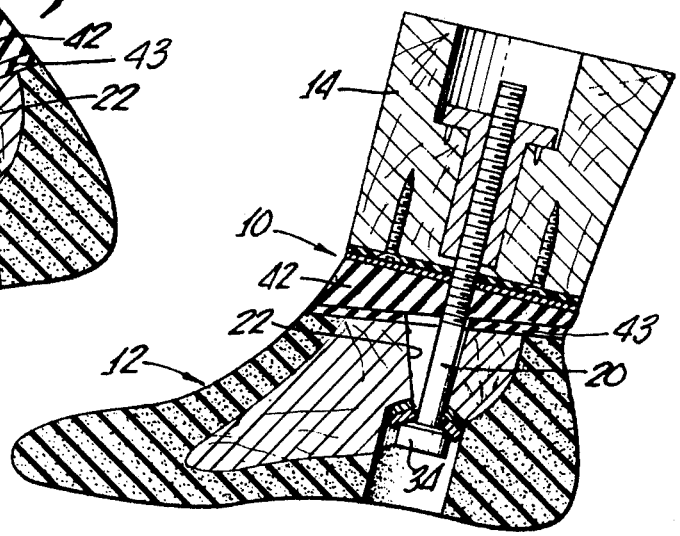
Figure 7:
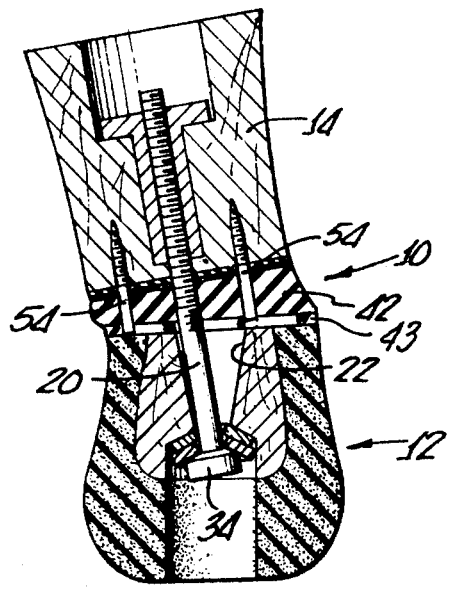
FIGS. 7 and 8 are views similar to FIG. 2, showing lateral angular movement of the lower leg with respect to the foot.
Figure 8:
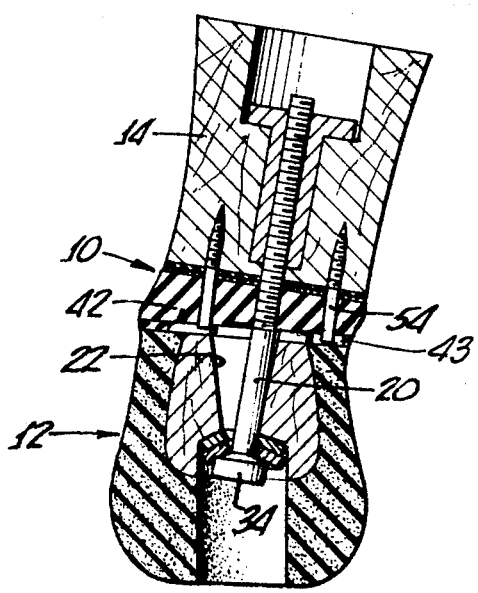

FIGS. 5 and 6 show the action of the ankle when walking. In FIG. 6, the wearer has placed his weight on the heel of foot 12, causing pad 42 to be compressed at its back end. In FIG. 5, the wearer has placed his weight on the "ball" of foot 12, compressing pad 42 at its front end. In FIGS. 7 and 8, the wearer has leaned the lower leg to one side and then the other, compressing the pad 42 on the inside of the lean.

Preferably, pad 42 is made of polyurethane in two different hardnesses, the front half 42a of the pad being harder than the rear half 42b. For example, the front half 42a might be 70 Shore hardness, while the rear half 42b might be 30 Shore hardness. For wearers of greater than average weight, the hardnesses might range up to 100–50, while for wearers of less than average weight, the hardnesses might be of the order of 40–20. Hardness of polyurethane is varied by adjusting the proportions of the two components which are mixed together prior to curing the material.

While I have shown and described in considerable detail what I believe to be the preferred form of my invention, it will be understood by those skilled in the art that the invention is not limited to such details, but might take various other forms within the scope of the claims.

What I claim is:

1. In combination with an ankle block forming the bottom end of a prosthetic lower leg, the said ankle block having a central threaded nut fixedly secured to the lower portion thereof with its threaded aperture opening downwardly, a foot and ankle prosthesis comprising, in combination:

a prosthetic foot having an inner keel of rigid material covered by foam elastomer molded into the form of a natural foot, said keel and elastomeric covering having an aperture formed therein extending upwardly from the bottom of the keel to the top surface of the keel, with an intermediate annular shoulder, and the top portion of the aperture being outwardly flared;

an attachment bolt passing upwardly through said aperture in the foot and screwed into said threaded nut on said ankle block, the bottom of said bolt including means to allow the bolt to move angularly and also rotationally with respect to the foot;

a pad of elastomeric material interposed between the top surface of the foot and the bottom surface of said block, said pad being of a thickness and hardness such that it can be compressed on one side or the other as the ankle block is leaned in that direction;

said elastomeric material being fixedly secured to the top surface of the foot, so that it becomes an integral part thereof;

a sheet of relatively rigid, low-friction material adhered to the top surface of said elastomeric pad, said sheet having sliding contact with the surface at the bottom end of said ankle block, and said sheet having at least one arcuate slot formed therein, the center of curvature of which is located at the center of said bolt;

the circumferential length of said slot being limited to approximately the normal angular range of movement of a natural foot; and at least one pin secured to said ankle block and projecting downwardly therefrom through said arcuate slot and into said pad of elastomeric material, said pin being movable with said ankle block to exert and maintain a torsional shear stress in the material when the ankle block is rotated with respect to the foot, whereby when the force causing relative rotation of the ankle block and foot is removed, said material under stress acts upon said pin to cause relative rotation of said block and said foot until a normal torsionally unstressed relative position therebetween is obtained;

said arcuate slot being engageble at its ends by said pin so as to limit relative rotation of the ankle block with respect to the pad of elastomeric material to a predetermined angular travel, whereby the elastomeric material is prevented from being overstressed and eventually destroyed.

2. The invention as defined in claim 1, wherein said means at the bottom end of said bolt comprises a bolt head seated on a pair of spherically cupped washers, one of which functions as a socket and the other as a ball, said one washer being seated on said annular shoulder.

3. The invention as defined in claim 1, wherein a plate of plastic material is cemented to the top surface of said prosthetic foot, covering said keel and foam elastomer, said pad of elastomeric material being cemented to the top surface of said plate; and said plate having at least one arcuate slot formed into which the bottom end of said pin projects; said arcuate slot in said plate being engageable at its ends by said pin so as to limit relative rotation of the foot with respect to the ankle block to a predetermined angular travel.

* * * * *